United States Patent
Duarte et al.

(10) Patent No.: US 10,383,740 B2
(45) Date of Patent: Aug. 20, 2019

(54) BONE GROWTH ENHANCING IMPLANT

(71) Applicant: Vivex Biomedical, Inc., Marietta, GA (US)

(72) Inventors: Luis E Duarte, San Angelo, TX (US); Jeffrey Scott Radcliffe, Marietta, GA (US)

(73) Assignee: Vivex Biomedical, Inc., Atlanta, GA (US)

( * ) Notice: Subject to any disclaimer, the term of this patent is extended or adjusted under 35 U.S.C. 154(b) by 264 days.

(21) Appl. No.: 15/142,160

(22) Filed: Apr. 29, 2016

(65) Prior Publication Data

US 2017/0312089 A1 Nov. 2, 2017

(51) Int. Cl.
*A61F 2/44* (2006.01)

(52) U.S. Cl.
CPC ...... *A61F 2/442* (2013.01); *A61F 2002/4475* (2013.01)

(58) Field of Classification Search
CPC .................................. A61F 2/44; A61F 2/442
See application file for complete search history.

(56) References Cited

U.S. PATENT DOCUMENTS

| | | | |
|---|---|---|---|
| 5,147,402 A | 9/1992 | Bohler et al. | |
| 6,468,311 B2 * | 10/2002 | Boyd | A61F 2/28 623/17.11 |
| 7,238,206 B2 | 7/2007 | Lange et al. | |
| 7,288,114 B2 | 10/2007 | Lange | |
| 8,016,887 B1 | 9/2011 | Castro | |
| 8,556,981 B2 | 10/2013 | Jones et al. | |
| 2003/0009235 A1 * | 1/2003 | Manrique | A61B 17/866 623/23.63 |
| 2008/0154377 A1 * | 6/2008 | Voellmicke | A61F 2/447 623/17.16 |
| 2008/0188945 A1 * | 8/2008 | Boyce | A61B 17/0401 623/23.61 |
| 2012/0330420 A1 * | 12/2012 | Brodke | A61F 2/30767 623/17.16 |
| 2014/0107786 A1 | 4/2014 | Geisler et al. | |

FOREIGN PATENT DOCUMENTS

JP 05176949 7/1993

* cited by examiner

*Primary Examiner* — Christopher Beccia
(74) *Attorney, Agent, or Firm* — David L. King

(57) ABSTRACT

An implant device having a non-conductive base structure with at least two exposed or exterior surfaces wherein at least one of the exposed or exterior surfaces has attained electrical conductivity on at least portions of the surface by an energy exposure wherein portions of the exposed or exterior surfaces are transformed by the energy exposure to attain the electrical conductivity.

5 Claims, 10 Drawing Sheets

BONE GROWTH ENHANCING IMPLANT

TECHNICAL FIELD

The present invention relates to implants generally, more particularly to implant devices that have enhanced recessed surface features that extend from inside the base structure of the implant to stimulate new bone growth formation on and into the implant.

BACKGROUND OF THE INVENTION

The use of skeletal implants is common in surgical repairs. Implants are employed in a variety of procedures such as spinal repair, knees, hips or shoulders and others. A common and most important feature of many implants is the integration of the implant into the skeletal structure. Mechanical fasteners, surface modifications, coatings, sutures and adhesives and other ways of affixing the device to the bone structure are used. These implants can be fashioned from human bone or other biological material or alternatively can be made from implantable grade synthetic plastics, ceramics or metals like stainless steel, titanium or the alloys of metals suitable for implantation.

One of the benefits of these plastic or metal implants is the strength and structure can be specifically designed to be even more durable than the bone being replaced.

As mentioned, one concern is properly securing the implant in place and insuring it cannot be dislodged or moved after repair. One of the best solutions to this issue is to allow the surrounding bone structure to grow around the implant and in some cases of hollow bone implants to allow new bone growth to occur not only around, but throughout the implant as well to achieve interlocked connectivity. Enhancing surface area by blasting, etching, or in some other way increasing the relative surface energy interface with the biologic component is desirable.

This is not particularly easy in many of the metal implants or hard plastic implants. In fact, the surface structure of the implant material is often adverse to bone formation. On some implant surfaces this may in fact be a desirable characteristic, but in those procedures where new bone growth formation is desirable this is problematic.

It is therefore an object of the present invention to provide an improved implant device that encourages new bone growth formation at selected surfaces of the device. The selected surfaces can be some or all external or internal exposed surface features of the implant device. The device with exposed surfaces that have selected surfaces for bone growth formation can be prepared by the methods as described below.

SUMMARY OF THE INVENTION

A spinal implant for insertion between two adjacent vertebrae has a body structure having load supporting exterior walls extending to a pair of load bearing outer surfaces, one being an upper surface, the other a lower surface; a cavity interposed between the load supporting exterior walls, the cavity being an opening through both load bearing outer surfaces; and a plurality of non-load bearing recessed projections. Each recessed projection extends from an interior surface of at least one load supporting wall into the cavity at an elevation above the lower surface and below the upper surface. Each projection has an enhanced osteoconductive treated exterior surface for the stimulation of new bone growth. Preferably, the enhanced osteoinductive treated exterior surface has a roughened surface or a textured surface or a bone mimicking surface or a coated surface of increased osteoinductivity.

The implant can be made from a non-conductive polymer and has one or more of the exterior surfaces of the projections laser etched to form electrically conductive pathways for new bone formation. The implant polymer can be polyether ether ketone (PEEK) or any other suitable implantable polymer.

The spinal implant has each of the recessed projections extend at least partly across the cavity toward an interior surface of an opposing exterior wall. In one embodiment, one or more of the recessed projections extends to an opposing interior wall to form a recessed strut. Each recessed strut can have a cross sectional shape in the form of opposing stepped plateaus. Each plateau has a planar top or bottom surface with the enhanced osteoinductive exterior surface wherein the cross sectional shape has a maximum width at a center of the strut and progressively narrower width at each subsequent adjacent stepped plateau. In another embodiment, the implant has three or more recessed struts, each adjacent strut having a different elevation. The three or more struts in combination form a cascading elevation highest at the center of the implant and lower toward ends. Alternatively, the three or more struts in combination form sequential rising elevations from one end toward an opposing end of the implant. Each recessed strut can have a rectangular or square cross section. Preferably, each recessed strut has a cross sectional width greater than its height, and wherein the exterior surfaces across at least the width is the enhanced osteoinductive treated exterior surface. In another embodiment, the implant has two pairs of recessed struts. Each strut in a pair is aligned and spaced apart to form an open pathway between the ends of the implant. This implant has a distal and a proximal end having a hole aligned with the pathway and configured to receive a guide wire.

Definitions

As used herein and in the claims:

"Exposed surface" means surfaces that are typically an outer or planar feature of 2-dimensions as used herein and throughout this description. "Exposed surface" means an outer skin or surface having a depth providing a 3-dimensional character, this depth being the distance the surface pattern penetrates into the body structure of the device to produce a roughened or textured pattern or coating for enhancing bone formation on the implant device. The exposed surface might also include an open trabecular structure wherein the voids extend from the surface throughout the structure. The exposed surface might also be defined in 4 dimensions, wherein time imposes specific and characteristic metabolic deposits which functionally mature the surface and guide phenotypic responses that are resonant with differentiated tissues and structures of the adjacent vertebral body.

"Mimetic patterns" mean to mimic a natural or man made or conceived pattern with the capability to replicate these patterns at an exposed surface to at least a depth sufficient to replicate at least the pattern.

BRIEF DESCRIPTION OF THE DRAWINGS

The invention will be described by way of example and with reference to the accompanying drawings in which.

DETAILED DESCRIPTION OF THE INVENTION

Figure 1:
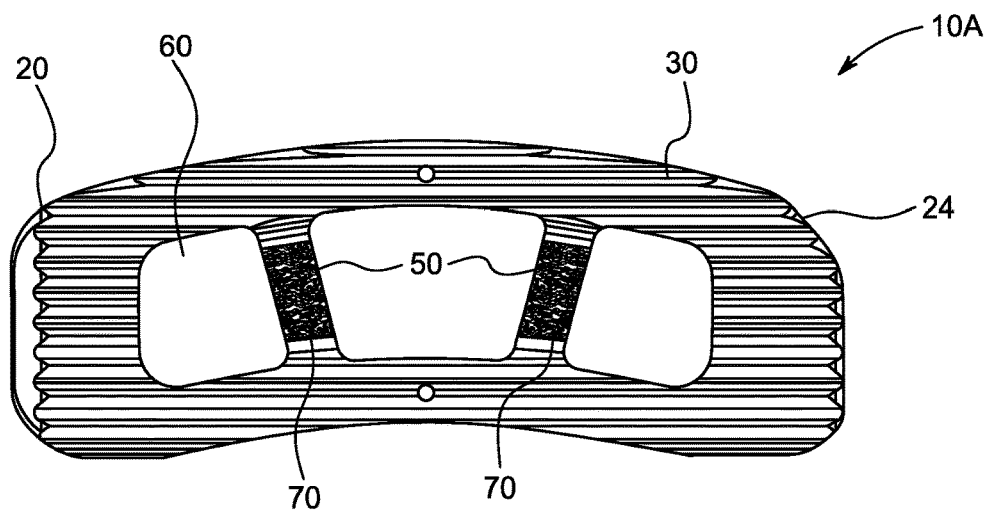
FIG. 1 is a top view of a first exemplary embodiment of the present invention.
Figure 1A:
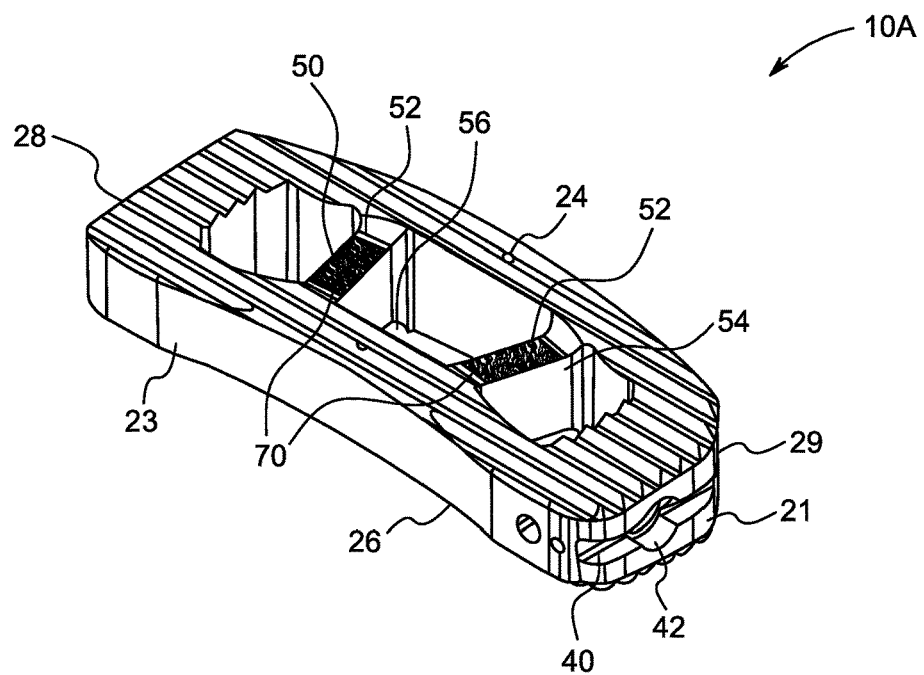
FIG. 1A is a perspective view of the first exemplary embodiment of FIG. 1.
Figure 5:
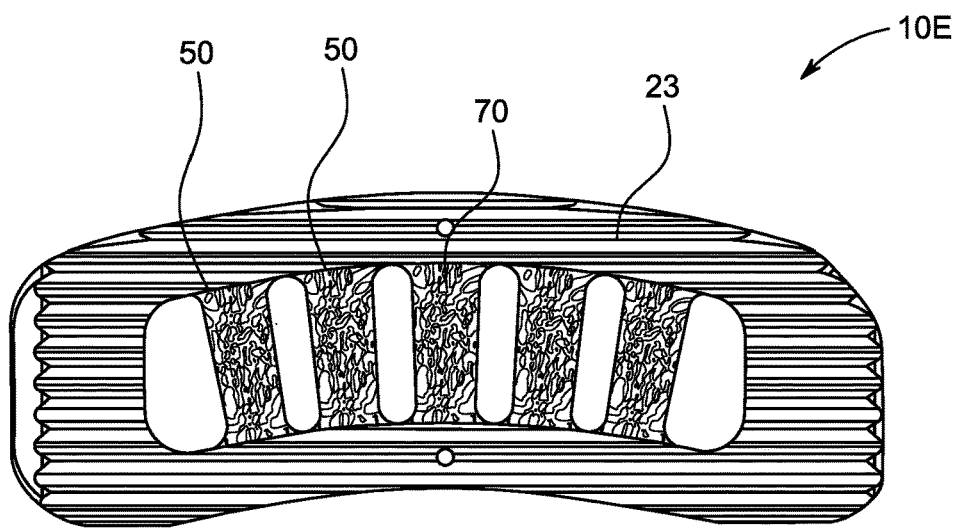
FIG. 5 is a top view of a fifth exemplary embodiment of the present invention.
Figure 5A:
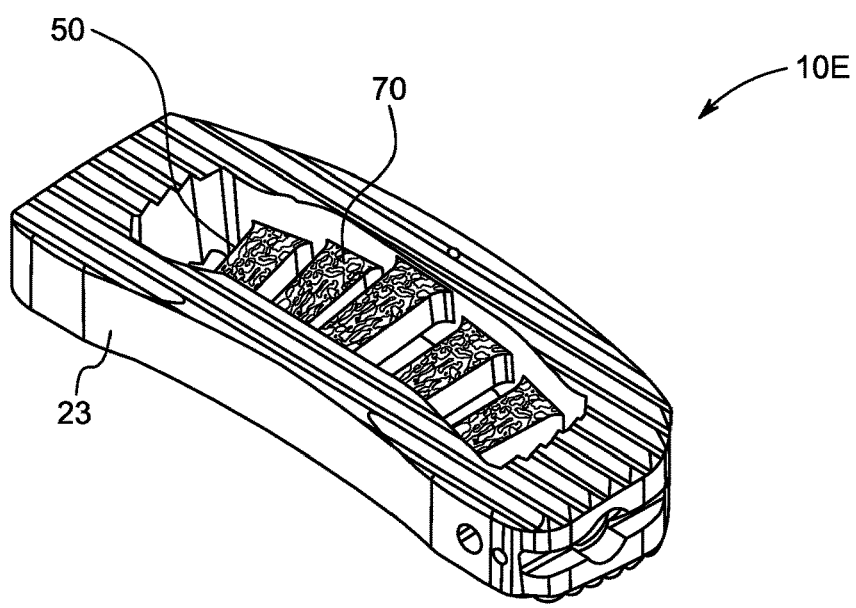
FIG. 5A is a perspective view of the fifth exemplary embodiment of FIG. 5.
Figure 6:
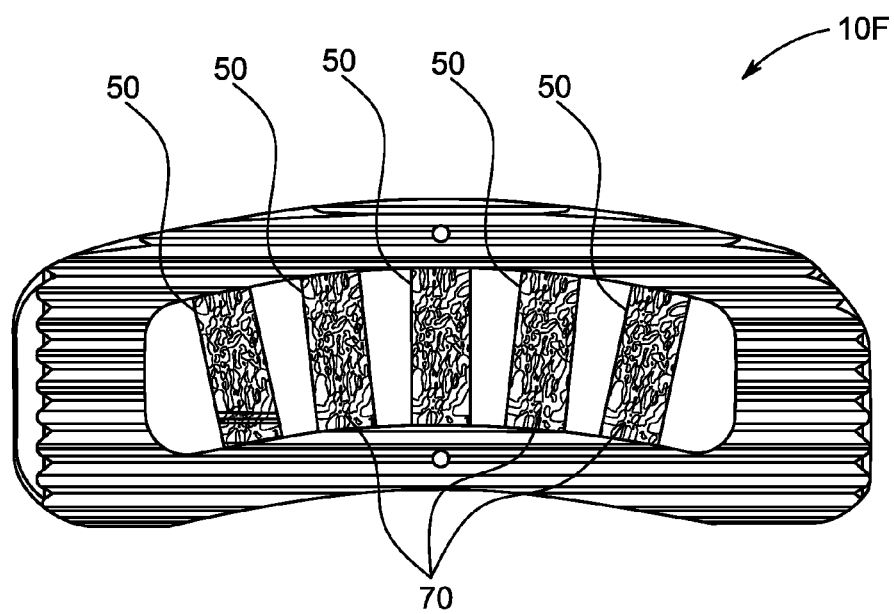
FIG. 6 is a top view of a sixth exemplary embodiment of the present invention.
Figure 6A:
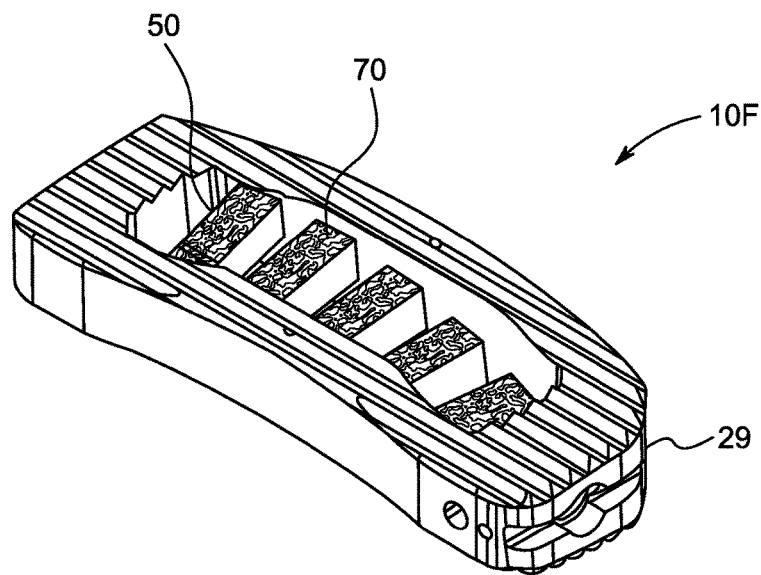
FIG. 6A is a perspective view of the sixth exemplary embodiment of FIG. 6.
Figure 6B:
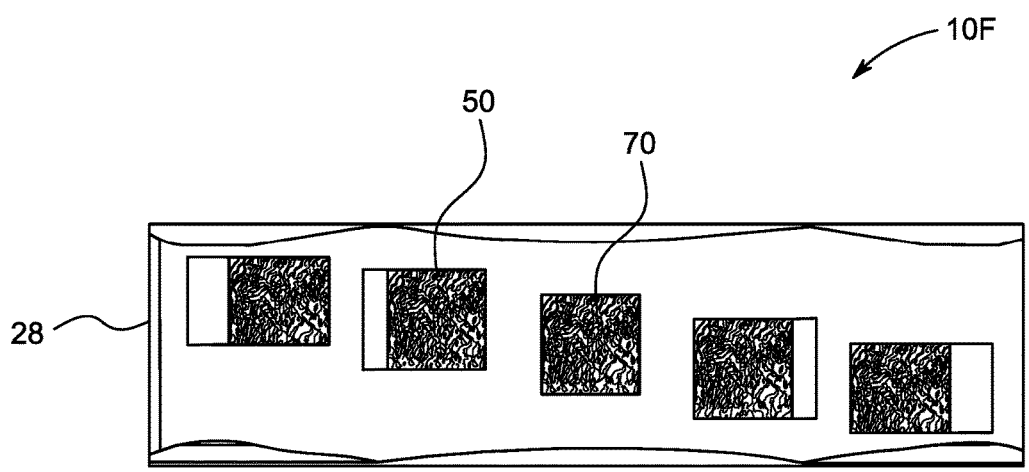
FIG. 6B is a partial section view taken along line 6-6 of FIG. 6.
Figure 7:
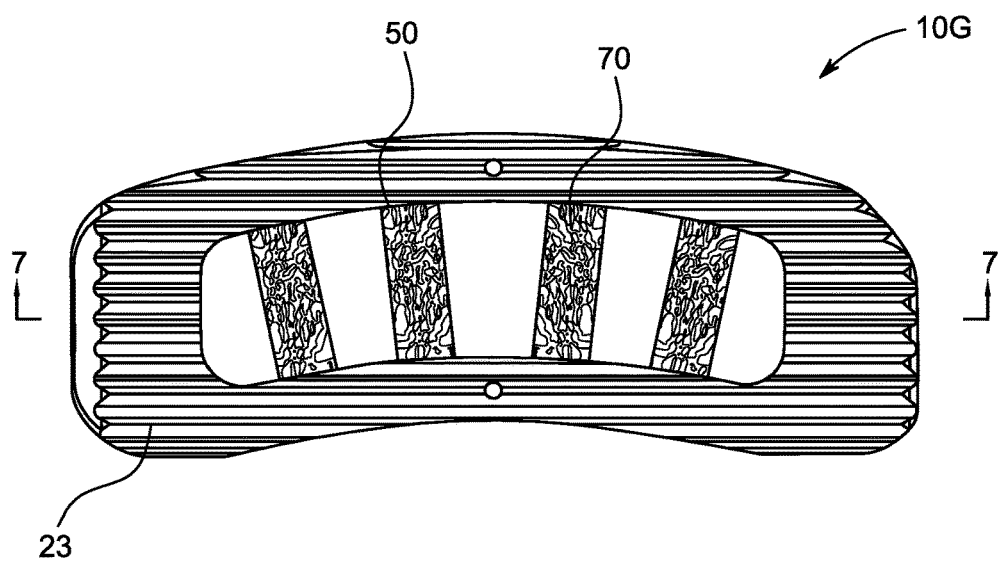
FIG. 7 is a top view of a seventh exemplary embodiment showing a recessed projection extending from a leading distal end, a trailing proximal end interior wall and recessed projections extending only partially across the cavity.
Figure 7A:
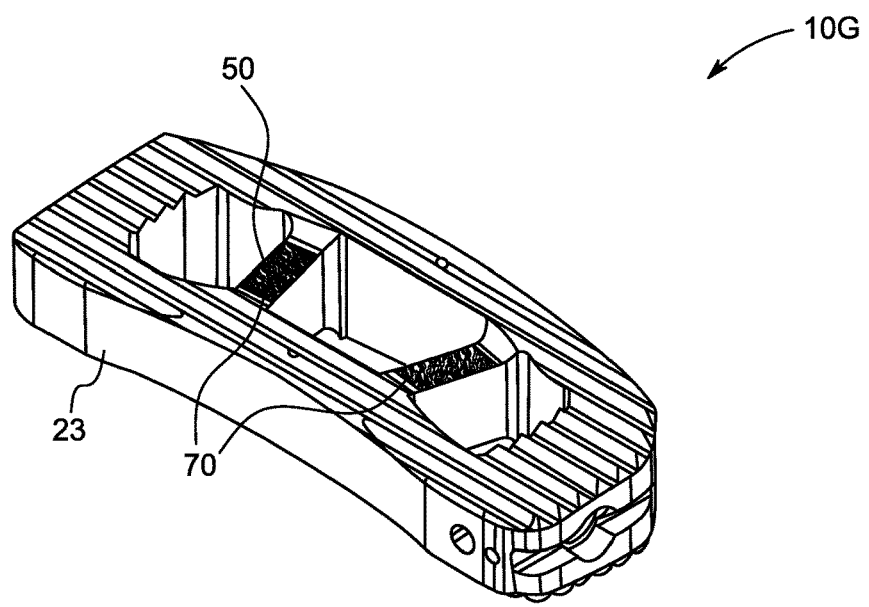
FIG. 7A is a perspective view of the seventh embodiment of FIG. 7.
Figure 7B:
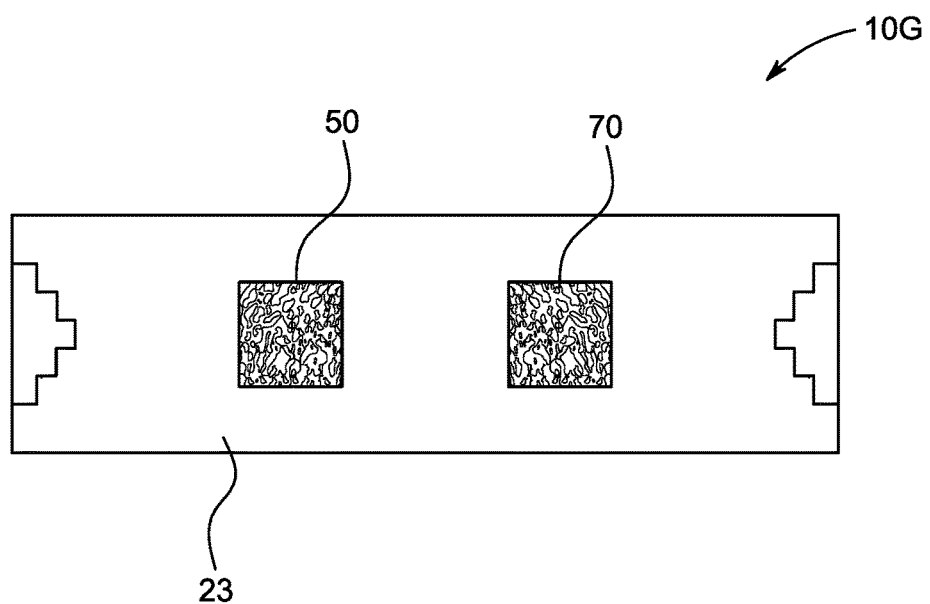
FIG. 7B is a cross section view taken along line 7-7 of FIG. 7.

With reference to the following drawings, several exemplary spinal implant embodiments are illustrated in FIGS. 1-7B. In each of the embodiments, the implants 10A-10G illustrate the same base structure. The base structure 20 includes an upper load bearing surface 24 and a lower load bearing surface 26. Interposed between the load bearing surfaces 24, 26 extend load bearing walls 23. The load bearing walls 23 extend around the periphery of the entire implant base structure 20. These load bearing walls and upper and lower load bearing surfaces support the weight of the adjacent vertebrae. As shown in each of the exemplary embodiments, the load bearing surfaces 24, 26 have a plurality of ridges 30. These ridges 30 provide gripping surfaces onto which the implant can be held tightly against the adjacent bone. Alternatively, roughened or other non-slip surfaces can be used. As further shown, in FIG. 1A, each implant body 20 has a proximal end 29 and a distal end 28. As illustrated, the proximal end 29 is shown having a slot 40 with a threaded opening 42. The slot 40 and the threaded opening 42 and the exterior surface of the end of the implant 21 allow an insertion tool (not illustrated) to be inserted such that when the implant is positioned between the vertebrae, the insertion tool can be used to hold the implant in place and push through an incision between the prepared vertebrae surfaces to position the implant 10A-10G into the prepared space between the adjacent vertebrae. As further illustrated, there is an enlarged cavity 60. The enlarged cavity 60 is an opening that extends between the upper surface 24 and the lower load bearing surface 26. This cavity 60 is a hollow opening across which a pair of recessed projections is illustrated. The projections 50 are shown recessed from both the upper outer surface 24 and the lower outer surface 26. These recessed projections 50 extend from one interior surface of the walls 23 of the implant as illustrated in FIGS. 1 and 1A, these projections 50 can extend to an opposing wall 23. When they extend to an opposing wall, the recessed projections 50 form struts across the implant body 20. With each of the exemplary implant embodiments shown it is noted that these recessed projections 50 can extend from one wall 23 and terminate not contacting an opposing wall 23. This is best illustrated in FIGS. 7-7B. It is important to note that the projections do not have to extend to both walls 23 in any of the various exemplary embodiments shown in FIGS. 1 through 6B. The implants 10A-10F, as illustrated, have the recessed projections 50 extend to both opposing walls 23. This is not a requirement as the projections 50 could extend only from one wall and project approximately half way or more towards the opposing wall. In any event, the recessed projections 50 whether formed as a strut contacting both walls 23 or simply as a projection extending from one wall 23 are recessed in such a manner that they provide no vertical load bearing support to the implant structure. When the projections 50 extend to both walls 23 and form struts they may have some stresses implanted along their length due to the support of the walls in terms of keeping the opposing walls aligned and together so they can't flex. In such a case the stresses or forces on the struts 50 are all longitudinally extending basically parallel to the vertebrae. However, depending on the thickness of the walls 23 around the periphery of the body 20 it is likely that no loads are applied onto the projections when formed as struts 50.

Most importantly, it is important to note that these recessed projections 50 provide exterior surfaces particularly on the top 52 and bottom 54 of the projections 50. These surfaces 52, 54 are exposed surfaces that are ideal for treatment. Additionally, the sides 56 of the projections 50 can equally be treated if so desired with an osteoconductive bone growth enhancing texturing, patterning or coating 70. The coating can be a biologic including stem cells and the texturing can be any type of roughened osteoconductive surface treatment including, but not limited to a mimetic pattern. It is important to note that these textured surfaces will increase the osteoinductive capability and enhance new bone growth and they do so in a rather efficient manner.

Each projection 50, as shown in the various embodiments, has at least one if not more than one of these surfaces 52, 54, 56 treated with an enhanced bone growth surface. This surface can be roughened or textured in such a fashion that new bone growth is actively encouraged to be initiated within the cavity 60 along these recessed exposed surfaces. What is unique about the present invention is that the exterior surfaces of the walls do not have to be treated with osteoinductive material, the objective is to ensure that the new bone growth formation is driven into the cavity 60, to encourage this it is the exposed surfaces 52, 54, 56 of the projections 50 that allow the osteoinductive capacity of the treated or patterned 70 surfaces to encourage the upper superior vertebrae or inferior vertebrae between which the implant is inserted to extend and grow into the cavity 60. Once the bone growth is created inside the cavity 60, an interlocking capability fuses the implant 10A-10G directly to the adjacent vertebrae. It is believed that by having the exposed surfaces of the projections 50 recessed and treated or patterned 70 in such a fashion that new growth formation is actually accelerated. Since there are no load bearing stresses within the projections 50, the material is simply in position to provide an enhanced bone growth capability.

Having only the projections 50 having exposed surfaces 52, 54, 56 treated or patterned 70 enables the rest of the implant device to be basically molded as is without any additional treatment. This is significant in that particular treatments in roughening of the material are quite expensive and time consuming. By limiting the surface area available for treatment or patterning 70, the cost of preparing an implant with improved osteoinductive capability is dramatically reduced. For example, the area needed to treat or pattern 70 the projections 50 is substantially less than a fraction of the overall surface of the implant. Thus, by selectively texturing and treating only that needed within the cavity 60 the cost of preparing such an implant is dramatically reduced. This enables implants to be used, preferably without any additional allograft material that is normally packed within the cavity 60. By avoiding this, the exposed surfaces become the conductive path for accepting and receiving an enhancing new bone growth formation. As the new bone growth forms in the recess it automatically interlocks the adjacent vertebrae into the cavity 60 of the implant both on the upper surface and lower surface as illustrated due to the fact that all the projections 50 are recessed.

Figure 2:
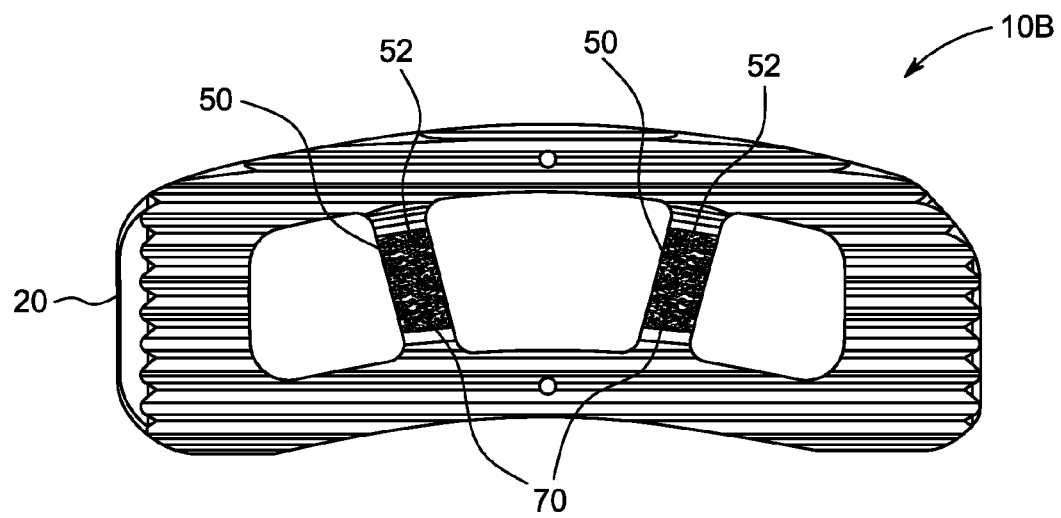
FIG. 2 is a top view of a second exemplary embodiment of the present invention.
Figure 2A:
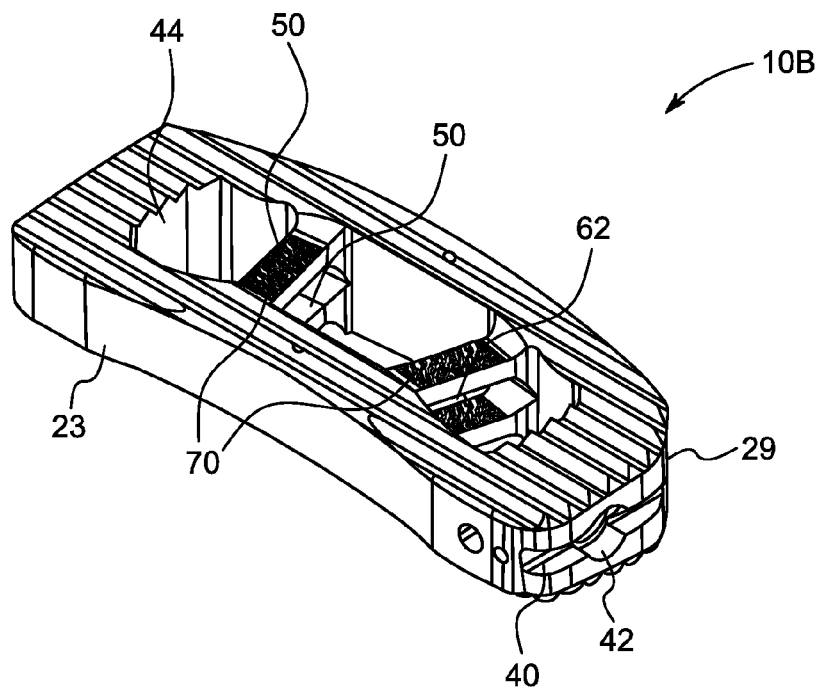
FIG. 2A is a perspective view of the second exemplary embodiment of FIG. 2.

With reference to FIG. 2, the implant 10B is illustrated having basically the same features as those illustrated in FIGS. 1 and 1A. The implant 10B, however, has the projections 50 formed as struts that are aligned in pairs creating a gap between the adjacent projections 50. As shown in FIG. 2A, this gap 62 ensures that the implant 10B is open between the struts 50. This is important in some embodiments wherein a guide wire can be positioned through an entire implant and the implant can be inserted between vertebrae using the guide wire as a path to ensure easy and proper placement of the implant device. To accomplish this feature the implant 10B has the opening 42 wherein the guide wire can pass through the opening 42 when an insertion tool that is cannulated is attached to the implant 10B. The guide wire than can be passed directly through the opening 44 such that the proximal end and the distal end are both guided through these openings by a guide wire, not illustrated. As shown, the projections 50 are similarly recessed and the exposed surfaces can be treated with the enhanced osteoinductive materials as previously mentioned.

Figure 3:
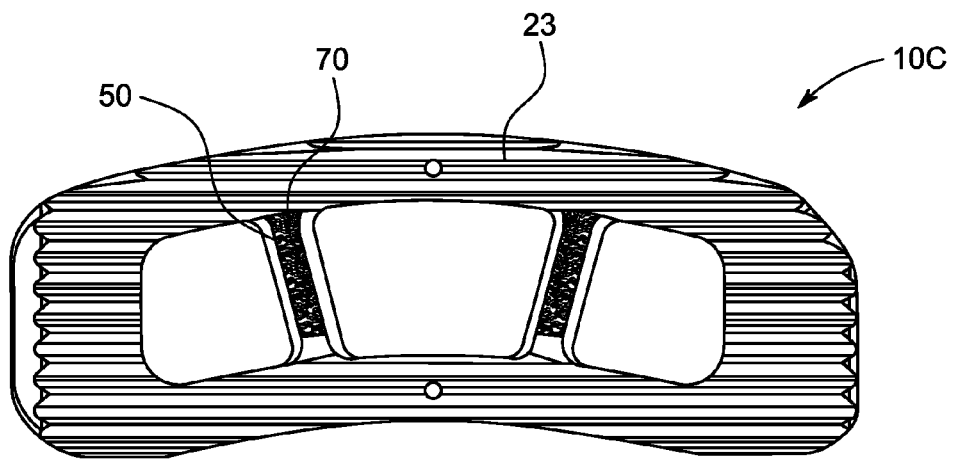
FIG. 3 is a top view of a third exemplary embodiment of the present invention.
Figure 3A:
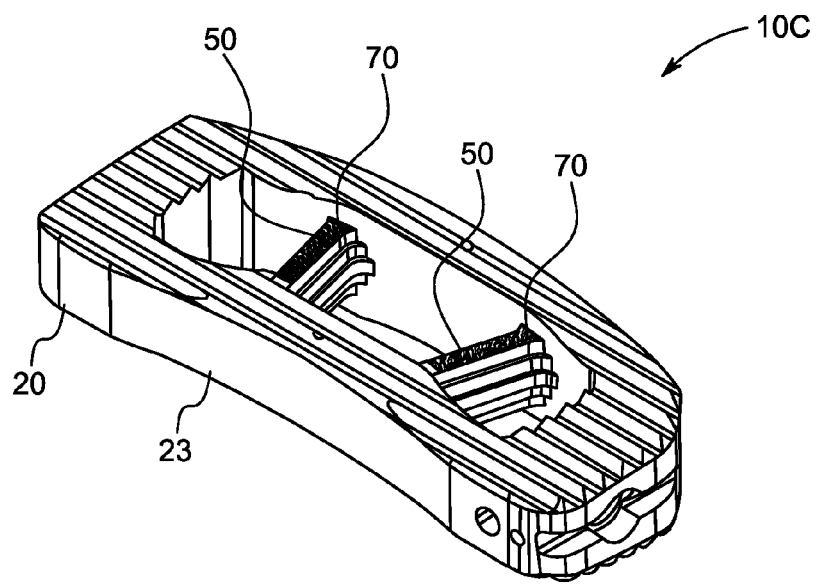
FIG. 3A is a perspective view of the third exemplary embodiment of FIG. 3.
Figure 3B:
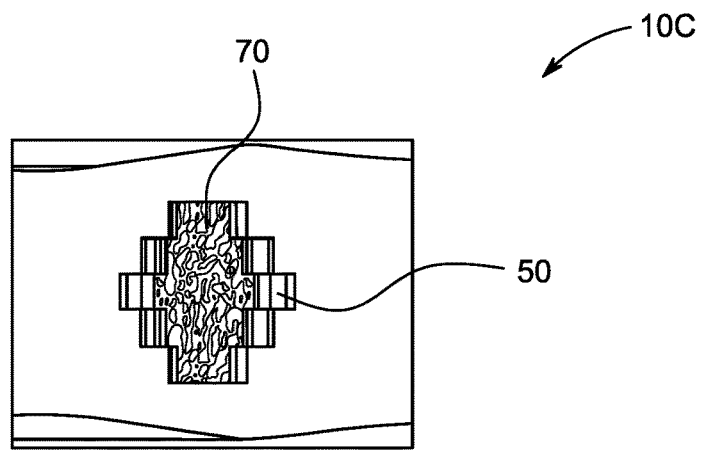
FIG. 3B is a partial section view taken along line 3-3 of FIG. 3.
Figure 4:
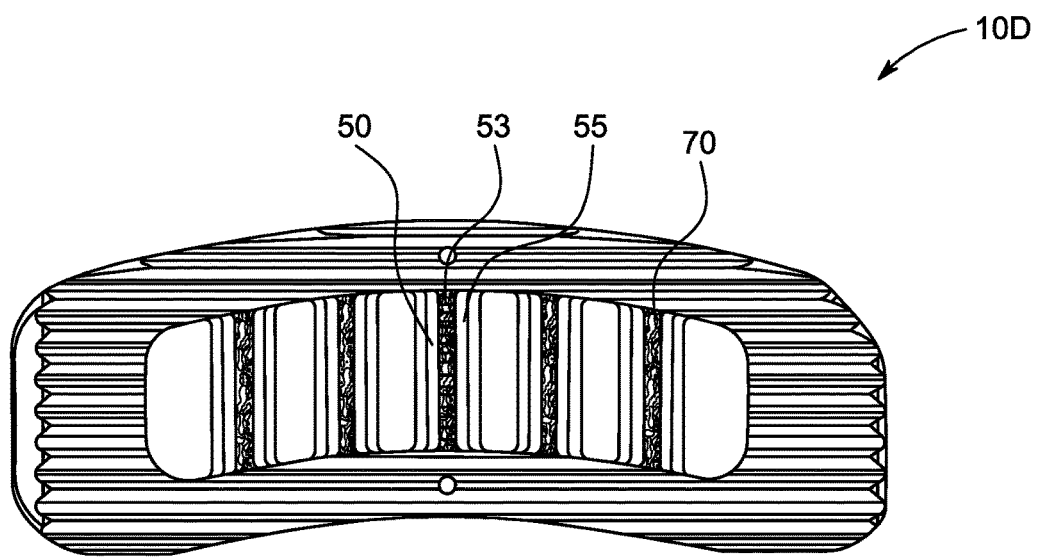
FIG. 4 is a top view of a fourth exemplary embodiment of the present invention.
Figure 4A:
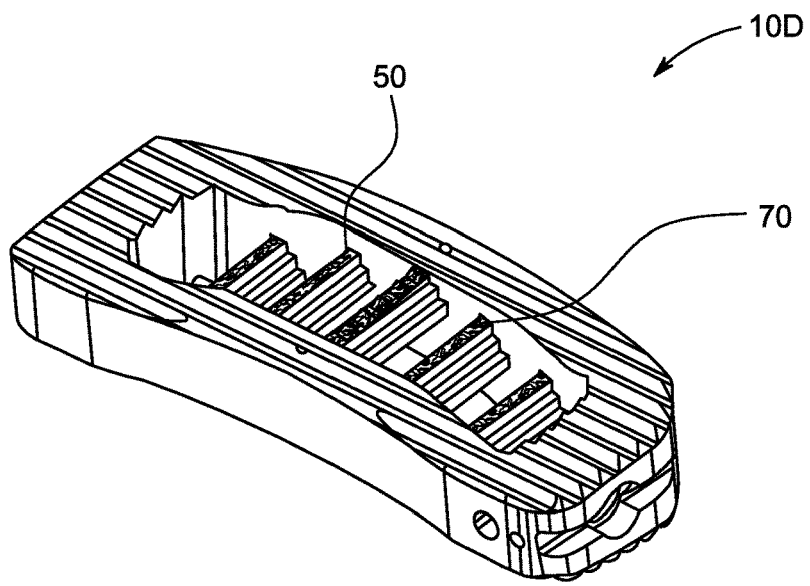
FIG. 4A is a perspective view of the fourth exemplary embodiment of FIG. 4.
Figure 4B:
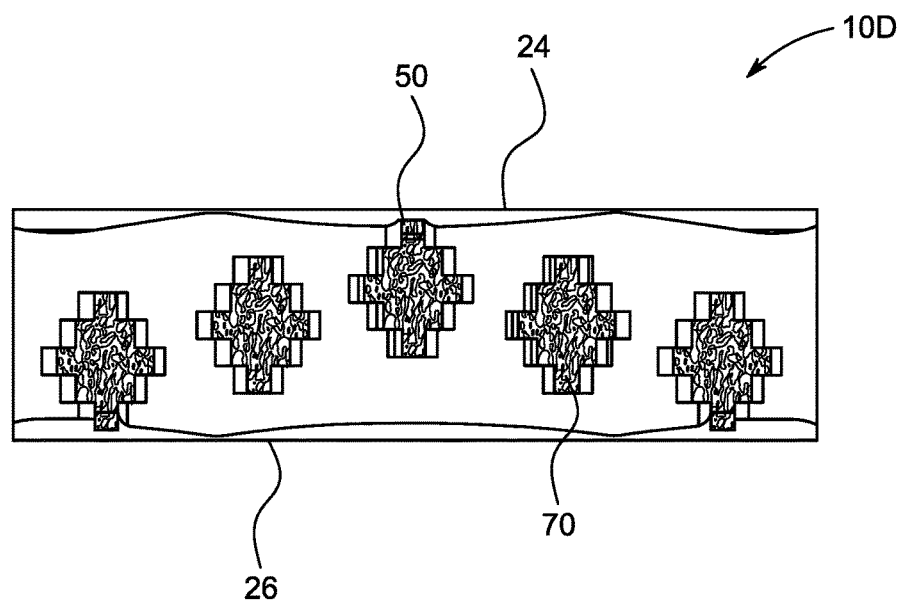
FIG. 4B is a partial section view taken along line 4-4 of FIG. 4.

With reference to FIG. 3, a modification to the implant 10C is shown wherein the recessed projection 50 is made in the form of struts wherein the struts have stepped plateaus as shown in the cross sectional view of FIG. 3B. This projection 50 provides a plurality of exposed surfaces onto which a texturing can be provided that will provide the enhanced bone growth. As illustrated, this projection 50 in the form of struts has a plurality of surfaces. The upper surfaces can be solid as illustrated or can have interruptions 53 as illustrated in FIG. 4. The interruptions 53 in the upper step 55 create additional locking capability for new bone growth.

With reference to FIG. 4, another embodiment using the same projections 50 as shown in FIG. 3A is illustrated. In this embodiment, the projections 50 are shown forming a plurality of struts across the cavity 60 wherein the struts are at different elevations relative to the upper surface 24 and the lower surface 26. What this enables the implant 10D to do is to get in close proximity and yet still be unloaded against the lower vertebrae at the lateral extremes wherein the center projection 50 is in closer proximity to the superior vertebrae. This enables the bone growth to occur in such a fashion that the lower bone can most rapidly enter in along the lateral extremes being enhanced by the treated surfaces wherein the center projection allows the superior vertebrae to grow towards the center. This creates an additional locking capability and is one way of making the implant device with enhanced osteoinductive capability.

Figure 5B:
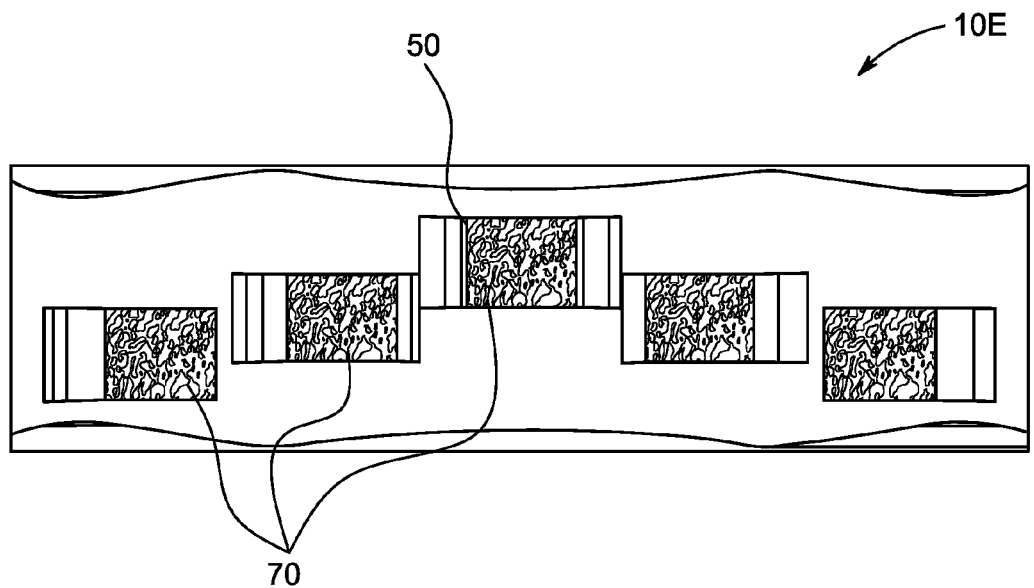
FIG. 5B is a partial section view taken along line 5-5 of FIG. 5.

With reference to FIGS. 5-5B, an alternative embodiment 10E is shown where the implant 10E has the struts 50 formed as substantially flat rectangular features. Again with the center element strut closer to the superior vertebrae and the lateral projections 50 shown closer to the inferior vertebrae. In this embodiment 10E, these rectangular projections 50 have flat planar surfaces with large exposed flat surface areas that are treated with the texturing, patterning, roughening or coating 70 on the exposed surfaces 52, 54 56 as selectively desired.

With reference to FIGS. 6-6B, an embodiment 10F similar to embodiment 10E is shown. This implant embodiment 10F has the features of the other devices however employs rectangular projections 50 that are provided in an increasing elevation from the proximal end 29 toward the distal end 28. This increasing staircase effect of the projections 50 allows the lower vertebrae to initiate bone growth toward the proximal end 29 and the upper vertebrae to initiate initial bone growth closer to the distal end 28. As such, as the bone grows, the new bone growth will secure itself within the cavity 60 in a progressive fashion across the exposed surfaces 52, 54, 56 of the device.

FIGS. 7-7B, illustrate an alternative embodiment 10G showing the projections 50 can be made as previously mentioned either from a lateral end extending from the interior surface of the supporting wall 23 or can be projections 50 extending toward the center line of the implant device from one wall 23, but not extend to the opposing wall 23. It is important to show this embodiment 10G applies equally to any of the embodiments previously shown such as the stepped plateau or a tapered cross section of the projection 50 can be produced having the bone growth enhancing features as previously discussed. However, the devices do not necessarily need to form struts in the sense that the ends can be truncated short of the opposing wall 23. This takes advantage of the capability of having a non-load bearing surface on implants that enhances bone growth, the inventors want to their device is not limited only to struts that contact both walls 23, but is contemplated to cover projections 50 that could extend only from one wall 23 or one end, but be treated in such a fashion that only the recessed surfaces have the treatment that can induce bone growth into the cavity 60.

Figure 8:
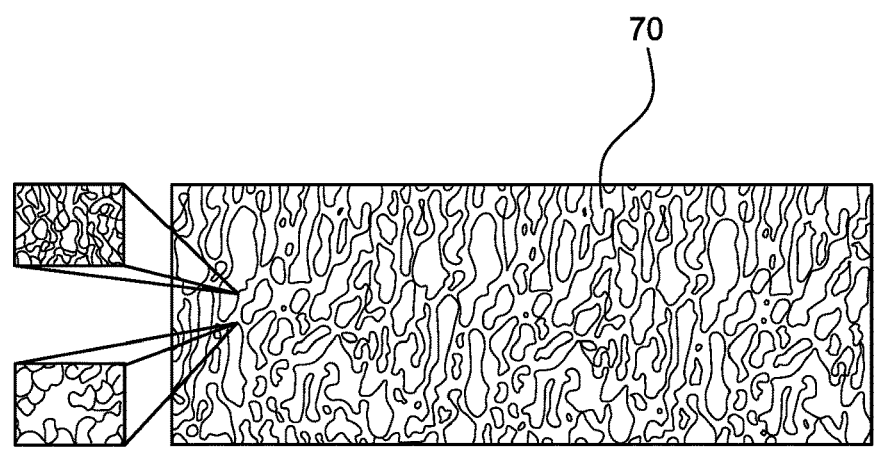
FIG. 8 shows an exemplary mimetic pattern.

With reference to FIG. 8, an exemplary mimetic pattern is illustrated.

Treatments can be coatings with stem cells or other biologically active material as taught in US 2013/0018471 and U.S. Pat. No. 8,679,189 which are each incorporated herein by reference in their entirety. Laser etchings or patterns forming electrically conductive pathways as taught in U.S. Pat. No. 8,679,189. Also by mechanical roughening to form a texturing or three dimensional effect, the depth being 150 microns or less. By material addition using 3-dimensional printing to form the porosity of the projections at the exposed surfaces.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A spinal implant for insertion between two adjacent vertebrae, the spinal implant comprising:
   a body structure having load supporting exterior walls extending to a pair of load bearing outer surfaces, one being an upper surface, the other a lower surface;
   an enlarged cavity interposed between and extending open to the load bearing outer surfaces of the load supporting exterior walls, the enlarged cavity being a hollow opening through both load bearing outer surfaces;
   a plurality of non-load bearing recessed projections within the hollow opening of the enlarged cavity, each recessed projection extending from an interior surface of at least one load supporting wall into the enlarged cavity at an elevation above the lower surface and below the upper surface, the plurality of recessed projections being in the form of struts extending from both interior surfaces of the walls or from along one interior surface of a wall, the strut being truncated short of the opposing wall; and
   wherein each recessed projection has an enhanced osteoconductive treated exterior surface for the stimulation of new bone growth, wherein the enhanced osteoinductive treated exterior surface being a roughened surface or a textured surface or a bone mimicking surface or a coated surface of increased osteoinductivity and wherein the load supporting exterior walls of the body structure have exterior surfaces not treated with an enhanced osteoconductive surface causing new bone growth between the two adjacent vertebrae to grow into the enlarged cavity to interlockingly fuse the implant directly to the adjacent vertebrae in the absence of packing the cavity with allograft material.

2. A spinal implant for insertion between two adjacent vertebrae, the spinal implant comprising:
   a body structure having load supporting exterior walls extending to a pair of load bearing outer surfaces, one being an upper surface, the other a lower surface;
   a enlarged cavity interposed between and extending open to the load bearing outer surfaces of the load supporting exterior walls, the enlarged cavity being a hollow opening through both load bearing outer surfaces;
   a plurality of non-load bearing recessed projections within the hollow opening of the enlarged cavity, each recessed projection extending from an interior surface of at least one load supporting wall into the enlarged cavity at an elevation above the lower surface and below the upper surface, the plurality of recessed projections being in the form of struts extending from both interior surfaces of the walls or from along one interior surface of a wall, the strut being truncated short of the opposing wall; and
   wherein each recessed projection has an enhanced osteoconductive treated exterior surface for the stimulation of new bone growth, wherein the enhanced osteoinductive treated exterior surface being a roughened surface or a textured surface or a bone mimicking surface or a coated surface of increased osteoinductivity and wherein the load supporting exterior walls of the body structure have exterior surfaces not treated with an enhanced osteoconductive surface causing new bone growth between the two adjacent vertebrae to grow into the enlarged cavity to interlockingly fuse the implant directly to the adjacent vertebrae, wherein the implant is a non-conductive polymer and has the exterior surfaces of the projections laser etched to form electrically conductive pathways for new bone formation in the absence of packing the cavity with allograft material.

3. The spinal implant of claim 2 wherein the implant is polyether ether ketone (PEEK).

4. The spinal implant of claim 1 wherein each of the recessed projections extend at least partly across the cavity toward an interior surface of an opposing exterior wall.

5. The spinal implant of claim 4 wherein one or more of the recessed projections extends to an opposing interior wall to form a recessed strut.

* * * * *